(12) United States Patent
Furness et al.

(10) Patent No.: US 6,659,936 B1
(45) Date of Patent: Dec. 9, 2003

(54) METHOD AND APPARATUS FOR TREATING INCONTINENCE

(75) Inventors: John B Furness, Fitzroy (AU); Robert W Barnett, Thornbury (AU); Helen E O'Connell, Parkville (AU); George D Hirst, South Yarra (AU)

(73) Assignee: University of Melbourne, Parkville (AU)

( * ) Notice: Subject to any disclaimer, the term of this patent is extended or adjusted under 35 U.S.C. 154(b) by 0 days.

(21) Appl. No.: 10/049,071

(22) PCT Filed: Aug. 4, 2000

(86) PCT No.: PCT/AU00/00925

§ 371 (c)(1),
(2), (4) Date: Feb. 4, 2002

(87) PCT Pub. No.: WO01/10357

PCT Pub. Date: Feb. 15, 2001

(30) Foreign Application Priority Data

Aug. 4, 1999 (AU) .............................................. PQ2026

(51) Int. Cl.[7] .............................. A61F 2/02; A61N 1/36
(52) U.S. Cl. .......................................... 600/30; 607/41
(58) Field of Search ................... 600/29–32; 607/40–41

(56) References Cited

U.S. PATENT DOCUMENTS

| | | |
|---|---|---|
| 3,870,051 A | 3/1975 | Brindley |
| 4,106,511 A | 8/1978 | Erlandsson |
| 4,153,059 A | 5/1979 | Fravel et al. |
| 4,256,093 A | 3/1981 | Helms et al. |
| 4,387,719 A | 6/1983 | Plevnik et al. |
| 4,580,578 A | 4/1986 | Barsom |
| 4,607,639 A | 8/1986 | Tanagho et al. |
| 4,688,575 A | 8/1987 | DuVall |
| 4,709,690 A | 12/1987 | Haber |
| 4,711,231 A | 12/1987 | Finegold et al. |
| 4,878,889 A | 11/1989 | Polyak |
| 5,117,840 A | 6/1992 | Brenman et al. |
| 5,199,430 A * | 4/1993 | Fang et al. ................... 607/40 |
| 5,370,671 A | 12/1994 | Maurer et al. |
| 5,478,305 A | 12/1995 | Craggs |
| 5,562,717 A | 10/1996 | Tippey et al. |
| 5,588,960 A | 12/1996 | Edwards el al. |
| 5,617,876 A | 4/1997 | Van Duyl |
| 5,620,475 A | 4/1997 | Magnusson |
| 5,667,615 A | 9/1997 | Maurer et al. |

(List continued on next page.)

FOREIGN PATENT DOCUMENTS

| | | |
|---|---|---|
| DE | 4436634 | 4/1996 |
| DE | 91522151 | 1/1997 |
| DE | 19750043 | 5/1999 |
| EP | 348114 | 12/1989 |
| FR | 2638964 | 5/1990 |
| PT | 101841 | 9/1996 |
| SE | 9301516 | 11/1994 |
| WO | WO 8401515 | 10/1983 |
| WO | WO 96/28211 | 9/1996 |
| WO | WO 9701309 | 6/1998 |
| WO | WO 98/23232 | 6/1998 |

OTHER PUBLICATIONS

Beard, J., "*Muscle Transplant Brings Relief From Incontinence,:*" New Scientist Magazine, vol. 150, Issue 2036, Jun. 29, 1996, pg. 20.

Primary Examiner—John P. Lacyk
(74) Attorney, Agent, or Firm—Akerman Senterfitt (57) ABSTRACT

An improved method, system and arrangement for treatment of urinary incontinence is disclosed, in which a portion of innervated smooth muscle (2) is transplanted and disposed around the urethra to provide a urethral sphincter (2). Electrical stimulation, by an implanted stimulator (1), maintains continuous tone in the sphincter. A remote controller (7) permits the sphincter (2) to be allowed to relax, and hence permit urine to flow out of the bladder.

178 Claims, 3 Drawing Sheets

U.S. PATENT DOCUMENTS

| | | |
|---|---|---|
| 5,676,160 A | 10/1997 | Bryant |
| 5,704,893 A | 1/1998 | Timm |
| 5,736,590 A | 4/1998 | Rasmussen |
| 5,755,758 A | 5/1998 | Woloszko et al. |
| 5,759,471 A | 6/1998 | Malewicz |
| 5,833,595 A | 11/1998 | Lin |
| 5,860,940 A | 1/1999 | Schönfeld |
| 6,086,525 A | 7/2000 | Davey et al. |
| 6,243,607 B1 * | 6/2001 | Mintchev et al. ............ 607/40 |
| 6,306,078 B1 * | 10/2001 | Lin ............................. 600/29 |
| 6,393,323 B1 * | 5/2002 | Sawan et al. ................. 607/41 |

\* cited by examiner

METHOD AND APPARATUS FOR TREATING INCONTINENCE

FIELD OF THE INVENTION

This invention relates to prosthetic devices for the treatment of urinary incontinence and, in particular, to prosthetic devices employing transplanted tissue.

BACKGROUND OF THE INVENTION

The present invention is concerned with forms of incontinence caused wholly or partly by inadequate sphincter function. This may include forms of stress incontinence, urge incontinence and total incontinence. The invention has been developed initially for use in treating male incontinence and will be described principally with respect to that application. However, it will be appreciated by those skilled in the art that the invention is also applicable for use in treating female incontinence.

Incontinence is a major health problem, particularly with the ageing population, for which there is no well-accepted medical treatment. For females, surgically constructed slings are increasingly being used for stress incontinence and with increasing success. However, here is no low risk and reliably effective treatment for moderate to severe male stress incontinence particularly after treatment of prostate cancer. As the incidence of prostate cancer is increasing, this is a growing health issue.

The internal sphincter of the urethra consists of smooth muscle cells interposed with elastic tissue and is located in the proximal urethra. Its constant tone is crucial to maintaining mechanical resistance in the proximal urethra sufficient to hold back the passive pressure exerted by urine in the bladder. Weakness in this area is a common cause of urinary incontinence, for example after treatment for prostate cancer.

Prosthetic sphincter valves have been proposed in numerous forms, including mechanical, hydraulic and electrical devices which replace or supplement the defective damaged internal sphincter of the urethra (e.g. PT 101841, SE 931516, GB 2266844, FR 2638964, WO97/01309 and U.S. Pat. No. 4,619,245). Electrical stimulation of the muscles of the sphincter has also been proposed (DE 29614895). Other approaches have proposed the use of external or implanted electrodes to stimulate existing sphincter function.

A variety of approaches have been proposed in relation to the electrical stimulation of the muscles of the sphincter, most of which are directed towards stimulating an existing sphincter and/or muscles disposed about, for example, a bladder(DE 29614895).

Another group of prior art proposals for the treatment of incontinence are directed towards the stimulation of sacral nerves and the like. Such proposals again seek to use the existing muscle structures. (U.S. Pat. No. 4,771,779, U.S. Pat. No. 4,703,775, U.S. Pat. No. 4,607,639, U.S. Pat. No. 3,870,051, U.S. Pat. No. 4,688,575, U.S. Pat. No. 4,389,719 and U.S. Pat. No. 5,702,428).

Other stimulation means have been proposed, for example U.S. Pat. No. 5,562,717, wherein stimulating electrodes are disposed on the skin of a person to externally stimulate existing muscles to control incontinence. This method is disadvantageous in that it requires electrodes to be disposed in a predetermined location of the person and be electrically connected to a power source therefore not allowing complete freedom.

It has also been proposed to implant part of a small skeletal muscle from the thigh around the patient's urethra, and then to electrically stimulate the muscle to "retrain" it to function as a replacement sphincter (New Scientist, Jun. 29 1996). However, this approach, even if successful, would require relatively high levels of electrical stimulation to allow sufficient contracture of the replacement sphincter.

It is an object of the present invention to provide an improved prosthetic device for use in treating incontinence.

SUMMARY OF THE INVENTION

Broadly, the present invention utilises innervated smooth muscle to provide an auxiliary sphincter. This is stimulated by a suitable device in order to provide a functional sphincter in the patient. As a consequence, the stimulator device can operate with lower power consumption, and produce a superior sphincter action.

According to a first aspect of the invention there is provided an implantable sphincter stimulator configured for operatively providing electrical stimulation to a surgically implanted innervated smooth muscle sphincter disposed about a urethra so as to control the flow of urine therethrough, the stimulator including:

a stimulus generating unit in electrical communication with a receiver, the stimulus generating unit operatively configured to provide a first predetermined electrical stimulation signal adapted to contract said sphincter, and a second predetermined signal adapted to allow said sphincter to relax, one of said predetermined signals being selected in response to a signal received at the receiver from a remote controller.

In preferred embodiments, the stimulator applies the first stimulation signal, unless a signal is received indicating that the patient wishes to empty the bladder. The second stimulation signal may be simply the absence of a stimulation, a lower level signal or an alternative signal.

Preferably, the stimulation signal is one which will maintain a continuous tone in the innervated sphincter. In other preferred embodiments of the invention the stimulation signal is pulsatile. Preferably, the stimulator provides multiple channel pulse generation. Preferably also, the stimulation pulse frequency is in the range of 0.25 to 2.5 Hz and having a width in the range of 0.05 to 0.20 milliseconds.

Preferably the stimuli applied have a current less than or equal to 30 mA. More preferably, the stimulation signal is generally rectangular and symmetrical biphasic, although alternative biphasic pulses may be used.

Preferably, the sphincter stimulator includes a replaceable or rechargeable battery power source, preferably one which is in-situ rechargeable, for example inductively.

Preferably, the signal to the receiver is communicated by microwave or radio means, optically or by magnetic energy and the receiver respectively is a microwave, radio, photon or magnetic energy receiver.

Preferably, the stimulus generating unit includes a demodulator responsive to the received signal for providing a modulated signal to a stimulus encoder which in turn provides a signal to a stimulus driver. The stimulator preferably includes two or more electrodes for operatively delivering the stimuli to the sphincter. The stimuli may differ between electrodes, or may be the same at each.

Preferably, after the sphincter has been relaxed, the stimulator is adapted to supply the first stimulation signal to contract the sphincter when a predetermined signal to contract the sphincter is not received by the receiver after a predetermined period.

Preferably, the sphincter stimulator includes a transmitter for transmitting sphincter stimulator telemetry information indicative of one or more parameters of the stimulator for detection remotely. Preferably, the information is transmitted by means of radio waves, microwaves, optically or by magnetic energy. More preferably, the parameters include one or more of the stimulation signal frequency, current, width and/or shape, and/or of the received signal strength and battery status. Preferably, the stimulus generating unit includes a processing device with non-volatile memory.

Preferably, the receiver is configured to accept a remotely generated sphincter stimulator calibration signal and in response, the stimulus generation unit selectively varies one or more of the stimulation signals. More preferably, the calibration signal is transmitted in response to received sphincter stimulator telemetry information, for example the telemetry signals from the stimulator.

Preferably, the stimulator is in electrical communication with the sphincter by at least one electrical lead having two or more electrodes which are operatively implanted into the sphincter at a predetermined location. More preferably, the lead includes three electrodes disposed in an epimysal, cuff or tripolar configuration about the sphincter.

Preferably, the smooth muscle is taken from the smooth muscle of the bladder and transplanted about the urethra and having its circulation intact. Alternatively, the muscle is venous smooth, anococcygeus smooth muscle, terminal ileum transplanted as a segment devoid of mucosa and having its circulation intact. A further alternative is the dartos smooth muscle from the scrotum or labia. In each case, the long axes of the muscle cells are disposed substantially circumferentially about the sphincter. Depending upon the muscle selected, the circulation may or may not be transplanted intact. If the circulation is not transplanted intact, new vessels will need to be regrown, or otherwise provided.

According to a second aspect of the invention there is provided a system for use in treating bladder incontinence in a person, the system including:

a portion of innervated smooth muscle tissue configured to define a sphincter and implanted substantially circumferentially about the urethra of the person;

an implanted sphincter stimulator arranged so as to allow electrical stimuli to be applied to the sphincter; and a non-implanted controller in communication with the sphincter stimulator for selectively triggering the generation of predetermined electrical stimulation signals to respectively contract the sphincter or allow the sphincter to relax.

Preferably, the smooth muscle is in the form of a strip and is generally rectangular. More preferably, the strip has dimensions in the range from 4.5 cm to 7.5 cm by 1.25 cm to 2.25 cm. Also preferable, the muscle is disposed substantially fully around the urethra in a generally cylindrical arrangement such that the long axes of the muscle cells are substantially circumferentially aligned.

Preferably, the smooth muscle is selected from those described above.

Preferably, the system includes a sphincter as described above.

Preferably, the controller includes:
a transmitter;
means for generating a predetermined signal at the transmitter;
a power source; and
actuation means for selectively generating a signal such that on receipt of the signal, the sphincter stimulator provides the stimulation signal at its output for contracting the sphincter or allowing it to relax. The signals for selecting relaxation or contracture may be different, or the same signal may trigger alternation of states.

One form of the controller, particularly for use by a physician, may include a receiver for receiving the sphincter stimulator telemetry information signal from the sphincter stimulator. Preferably, the signal is transmitted by radio waves, microwaves, optically or by magnetic energy and receiver respectively is a radio, microwave, photon or magnetic energy receiver.

Preferably, the system includes a remote sphincter stimulator programming unit for selectively programming the sphincter stimulator to provide a predetermined output. Preferably, one or more of the stimulation signal current, shape, frequency and width is variable in response to the calibration signal provided by the programming unit. More preferably, the programming unit includes a transceiver for providing the programming signal to the stimulator. The programming unit may conveniently be the physician controller.

According to a third aspect of the invention there is provided a method of using an implantable sphincter stimulator for treating bladder incontinence, the method including the steps of disposing an innervated smooth muscle sphincter about a urethra, arranging one or more electrodes so as to allow stimulation of the neural structures of said sphincter, said electrodes being connected to the sphincter stimulator, so that post implantation, a predetermined stimulation signal may be applied by a stimulus generating unit to selectively contract the sphincter or allow it to relax.

Preferably, the method includes the step of transmitting the signal to the sphincter stimulator by radio signals, microwaves, optically or by magnetic energy.

Preferably, three electrodes are arranged in the sphincter in an epimysal, cuff or tripolar configuration.

Preferably, the sphincter is smooth muscle selected from those previously described.

According to a fourth aspect of the invention there is provided a method of treating incontinence including the steps of:

disposing an innervated smooth muscle sphincter around a urethra;

locating a plurality of electrodes in predetermined locations in the sphincter and electrically connecting the electrodes with an implanted sphincter stimulator; and selectively actuating the sphincter stimulator to provide a predetermined stimulation signal to either contract the sphincter or allow it to relax in response to a remotely generated signal.

According to another aspect of the invention there is provided a method of surgically implanting a sphincter stimulator in a system for treating urinary incontinence, including the steps of:

implanting the innervated smooth muscle sphincter about the urethra in a person;

implanting the electrodes into the sphincter at predetermined locations; and implanting the sphincter stimulator, the arrangement being such that the electrodes are electrically connected to the sphincter controller to permit stimulation signals from said sphincter stimulator to stimulate the neural structures of said smooth muscle.

Implanting in this context includes transplanting from the same or another person, or the use of externally prepared smooth muscle tissue. In each aspect, it is preferred that the implanted sphincter function so as to substantially prevent leakage of urine when contracted. In general, the main function of the innervated muscle prosthesis is to augment function in the internal sphincter. It should not be used to override any natural sphincter function that may be preserved. The sphincteric pressure exerted by the prosthesis should be sufficient to restore the net sphincteric resistance to its normal level of operation. Unnecessarily high pressure would not only be wasteful of internal stimulator energy but could also cause dangerous overfilling of the bladder. On the other hand, the pressure must be sufficiently high to prevent the leakage of urine.

The smooth muscle tissue may be selected from those described above, or any other suitable smooth muscle tissue. It will be appreciated by those skilled in the art that other types of smooth muscle may potentially be employed as the implantable sphincter including alpha-adrenergic excitatory innervation, cholinergic excitatory or, inter alia, circular intestinal muscle.

One advantage of using smooth muscle tissue is that it physiologically performs a sphincteric-like function and the muscle layer should be able to be transplanted whilst maintaining its innervation, or allowing for its reinnervation, and blood supply. Moreover, smooth muscle of the types described is readily reinnervated by sympathetic nerves should the existing innervation be damaged during surgery. Reinnervation may take some time, for example, two to three weeks, after surgery.

Another advantages associated with the use of an innervated smooth muscle sphincter in accordance with the present invention is that in smooth muscle, a long-lasting contracture (2–3 seconds) results from a single neural stimulation. Accordingly, only a low frequency of stimulation is required to produce a tetanic contraction especially where it is moderated by neurotransmitter release.

The tension generated per unit cross-sectional area of smooth muscle is greater than for skeletal muscle. Smooth muscle generates tension over a wide length/tension relationship, that is, it continues to generate tension even when partially contracted. Smooth muscle is able to maintain high tension with relatively low energy expenditure. Smooth muscle tissue generally displays a persistent generation of tone during low frequency repetitive nerve stimulation.

A further advantage of the use of smooth muscle according to the present invention is that low frequency nerve stimulation causes the release of a chemical transmitter. Stimulating the nerves within smooth muscle invariably triggers a contraction because the neurotransmitter interacts with a receptor. The activated transmitter/receptor complex then activates a second messenger pathway and releases calcium ions from internal stores. It is relevant that calcium is the final trigger in the contraction of both skeletal, smooth or cardiac muscle. When stores release calcium they do so for extended periods of time, typically in the order of several seconds. Therefore, if the exciting pathway is triggered repeatedly at low frequencies a sustained rise in calcium occurs and the smooth muscle develops a contracture. That is, it does not relax between stimuli. In some smooth muscles, a few stimuli delivered every two seconds, for example, will lead to a sustained contraction.

An alternative way to excite smooth muscle is to stimulate it directly which produces quite long lasting contractions but only on application of very high stimulating voltages. Nerves have low thresholds for activation, compared with muscles, and this, together with the low frequencies of activation required, means that stimulus spread will be avoided. Importantly, an electrical device can reasonably be expected to survive untouched for many years with such low usage demands.

BRIEF DESCRIPTION OF THE DRAWINGS

A preferred embodiment of the invention will now be described, by way of example only, with reference to the accompanying drawings in which.

DETAILED DESCRIPTION OF PREFERRED EMBODIMENTS

Referring in general to FIGS. 1 to 6, there is illustrated an implantable sphincter stimulator 1 for selectively providing electrical stimulation to an innervated smooth muscle sphincter 2 disposed about a urethra 3 for controlling the flow of urine.

Figure 1:
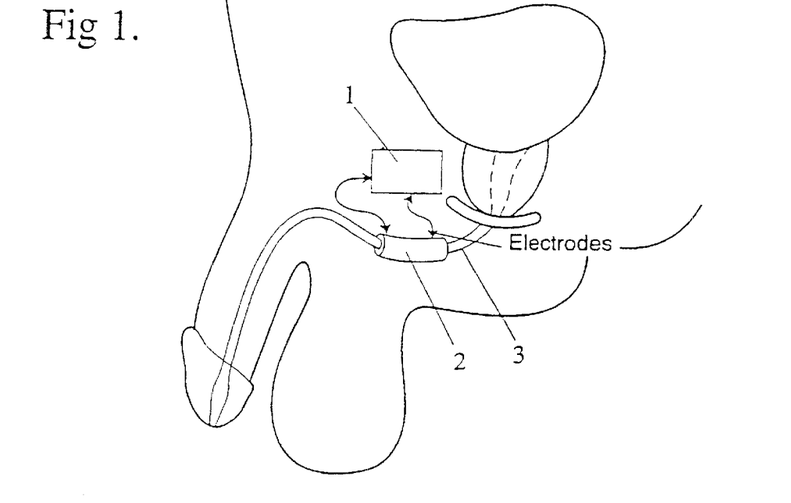
FIG. 1 is a schematic illustration of a system for treating incontinence according to the invention.

Stimulator 1 includes a signal processing unit 4 in electrical communication with a receiver 5. Signal processing unit 4 is configured to provide a predetermined electrical stimulation signal at a first output 6 of stimulator 1 in response to a signal generated remotely by controller 7 and applied at receiver 5 such that processing unit 4 selectively provides the stimulation signal to either contract sphincter 2 to substantially block the flow of urine along the urethra 3 or to allow sphincter 2 to relax and allow urine to flow.

Figure 2:
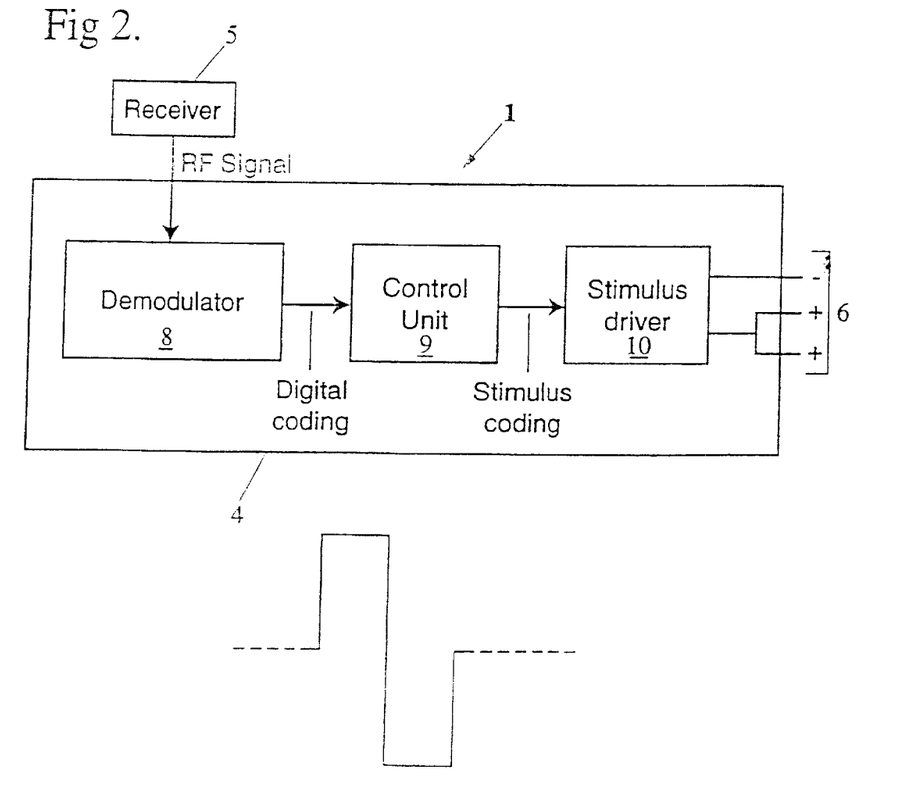
FIG. 2 schematically illustrates the implanted sphincter stimulator of FIG. 1.

Referring to FIG. 2 particularly, signal processing unit 4 includes a demodulator 8 responsive to the signal received at receiver 5 for providing a modulated signal to a stimulus encoder 9 which in turn provides a signal to a stimulus driver 10 which provides the stimulated signal at sphincter stimulator output 6.

Once sphincter 2 is allowed to relax, processing unit 4 includes means to supply a stimulation signal at output 6 to contract sphincter 2 when a predetermined signal to contract the sphincter is not received by signal processing unit 4 via receiver 5 for a predetermined time period. In the preferred implementation, the processing unit 4 provides stimuli adapted to contract the sphincter unless a signal is received, in response to which the stimuli is turned off, and the sphincter relaxes.

The signal is communicated to sphincter stimulator 1 by means of radio frequency waves and receiver 5 is an RF receiver. If the casing of the stimulator is made of titanium, and the receiver is inside, then a frequency of 8–10 kHz is preferred. If the casing is made of silicone rubber or the like, then 8–10 MHz is preferred.

In other embodiments of the invention, the signal may be communicated optically in the range 630 nm to 1400 nm to sphincter stimulator 1 and receiver 5 is a photon detector in the form of a PMT, photo-diode or other suitable detector.

In yet other embodiments of the invention, the signal is communicated to sphincter stimulator 1 by microwave means and receiver 5 is a microwave receiver. In such embodiments, the microwave signal has a frequency in the range of 0.9 to 2.5 GHz. Alternatively, the signal is communicated to sphincter stimulator 1 by magnetic means and receiver 5 is a magnetic energy receiver. Any other suitable communication arrangement may be used.

Figure 3:
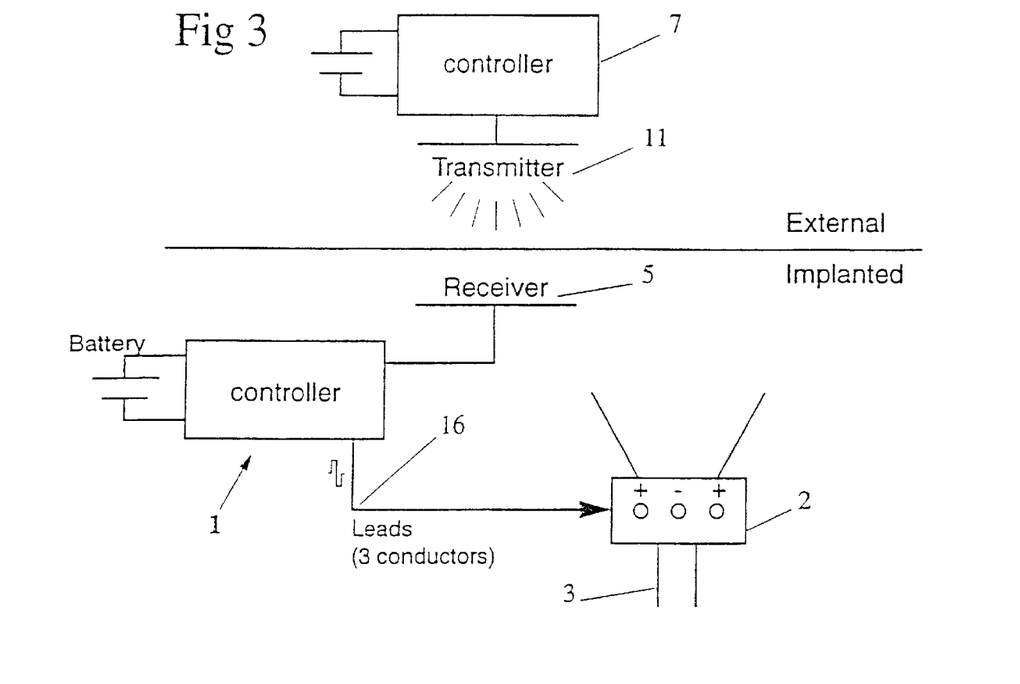
FIG. 3 schematically illustrates external and implanted parts of the system of FIG. 1.

As is best illustrated in FIG. 3, controller 7 includes the RF transmitter which is driven by a means for generating the control signal. Controller 7 further includes actuation means for selectively generating the control signal at transmitter 11.

Part of transmitter 11 is also a receiver for receiving an information signal indicative of at least one parameter of the sphincter stimulator and provided by the sphincter stimulator. The telemetry information signal is transmitted to the controller by means of a transmitter disposed within receiver 5. In embodiments of the invention where microwaves are employed to communicate either the control signal or telemetry information signal, transceiver 11 of controller 7 is configured to transmit and receive microwave radiation. In embodiments where the control signal is transmitted optically, transceiver 11 includes a photon detector in the form of a PMT or solid state device and a light source having a predetermined output. In embodiments of the invention where the control signal and the sphincter stimulator information signal are transmitted by magnetic energy, the transmitter receiver 5 functions as a passive proximity card and controller 7 functions as the active proximity card reader.

FIG. 2 illustrates a stimulation signal in the form of a pulse. The pulse is generally rectangular and symmetrically biphasic. In other embodiments of the invention, not illustrated, sphincter stimulator 1 provides multiple channel pulse generation at output 6. The stimulation signal is selected so as to provide a substantially continuous tone in the sphincter.

The stimulation signal provided at output 6 has a substantially constant current less that or equal to 30 mA, and preferably of the order of 15 mA. The stimulation pulse frequency provided to sphincter 1 by output 6 is in the range of 0.25 Hz to 2.5 Hz and is preferably 2 Hz. The stimulation pulse width is in the range of 0.05 ms to 0.2 ms and is preferably 0.15 ms. It should be noted that the device is current regulated, and accordingly the stimulation voltage will vary with the resistance of the muscle tissue between the electrodes. Typical values for the voltage are between 0.2 and 7 volts.

It should be noted, however, that these parameters are variable and are configured for each person.

Preferably, the smooth muscle is taken from the smooth muscle of the bladder and transplanted about the urethra and having its circulation intact.

Alternatively, the muscle may be venous smooth, anococcygeus smooth muscle, terminal ileum transplanted as a segment devoid of mucosa and having its circulation intact. A further alternative is the dartos smooth muscle from the scrotum or labia. Any other suitable muscle may be employed. In each case, the long axes of the muscle cells are disposed substantially circumferentially about the sphincter.

The muscle is generally in the form of a rectangular strip such that the long axes of the muscle cells are disposed substantially lengthwise along the strip. The muscle is then disposed substantially fully around the urethra in a generally cylindrical arrangement such that the long axes of the muscle cells are substantially circumferencially disposed about the urethra. Preferably, the strip is completely disposed around the urethra.

The muscle strip has dimensions 6 cm by 2 cm and is preferably provided in the range from 4.5 cm to 7.5 cm by 1.25 cm to 2.25 cm.

Figure 6:
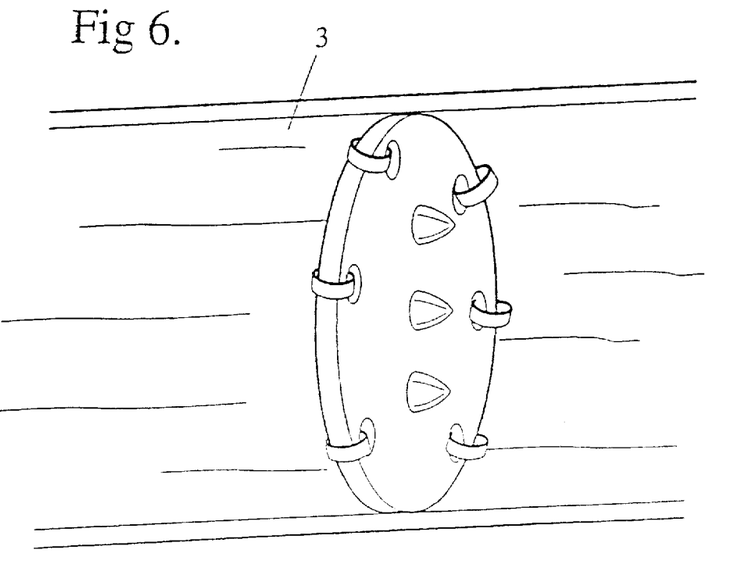
FIG. 6 is an enlarged view of the electrode configuration of FIG. 5.

The stimulation signal is provided at output 6 of sphincter stimulator 1 is supplied to sphincter 2 by an electrode implanted into the sphincter at a predetermined location and an electrical lead 16 being disposed intermediate. As is best illustrated in FIG. 6, lead 16 includes three electrodes disposed in a tripolar configuration about sphincter 2 and having means to electrically connect to lead 16. In other embodiments of the invention, the three electrodes are disposed in a cuff or epimysal configuration about the sphincter.

Electrode leads may extend between the pulse generator and the electrodes, allowing some "slackness" in their length to account for normal body to movements.

Figure 5:
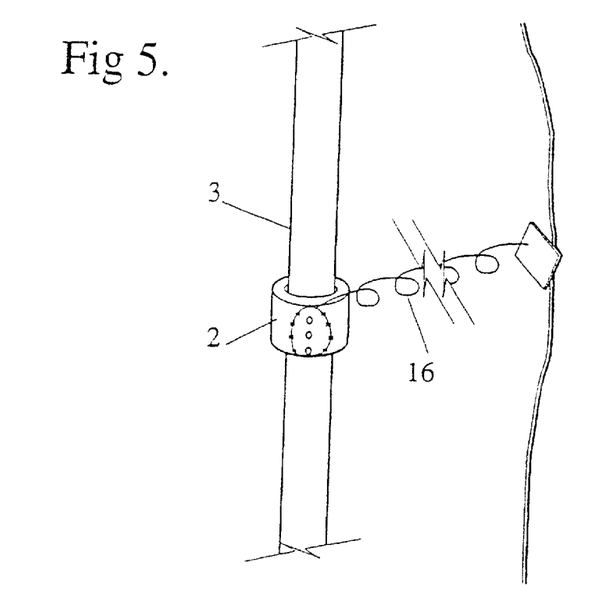
FIG. 5 is an alternative schematic illustration of the system of FIG. 1 showing a preferred configuration of electrodes.

As is best illustrated in FIGS. 5 and 6, the configuration of the electrodes are disposed in a tripolar configuration. Simple tripolar electrodes are the least expensive alternative, are relatively easy to implant and can be used to stimulate the transplanted smooth muscle. Their exposed metallic surfaces usually consist of a cathode aligned between two anodes.

In the epimysial configuration, the electrodes are sutured directly onto the surface of a muscle. These electrodes are implemented when stimulation of a motor nerve trunk is impractical, however, this is not necessarily always the case.

In the cuff electrode configurations are employed in alternative embodiments and are contained within an insulating sheath substantially circumferentially around the circumference of the transplanted sphincter. They are capable of stimulating the embedded nerve fibres maximally while keeping the stimulus field local to the transplant.

In other embodiments of the invention, not illustrated, the sphincter stimulator includes a second output such that one of the sphincter stimulator outputs provides a signal to contract the sphincter and the other output provides a stimulation signal to allow the sphincter to relax or contract to a lesser extent. In this embodiment, each of the first and second outputs of the sphincter stimulator each include a lead having three outputs in a tripolar configuration about the sphincter. In yet other embodiments, the first and second outputs each include a lead having three electrodes disposed in a cuff or epimysal configuration about the sphincter.

It will be appreciated that in normal use, only two of the three electrodes will be used to deliver stimuli. The third electrode is provided as a spare, in the event that one of the electrodes ceases to function. However, it is contemplated that the present invention could use a more complicated set of stimuli, or more electrodes.

Sphincter stimulator 1 includes a replaceable battery power source 17, not illustrated in FIG. 2. In one implementation, battery 17 is in electrical communication with signal processing unit 4 such that the control signal provided by controller 7 to sphincter stimulator 1 inductively provides energy to recharge the battery. In another implementation, in the case of radio frequency transceiving between the and sphincter stimulators, the signal is provided by modulating the RF signal such that the signal processing unit extracts the control signal and provides the battery with remaining power from the RF signal.

Figure 4:
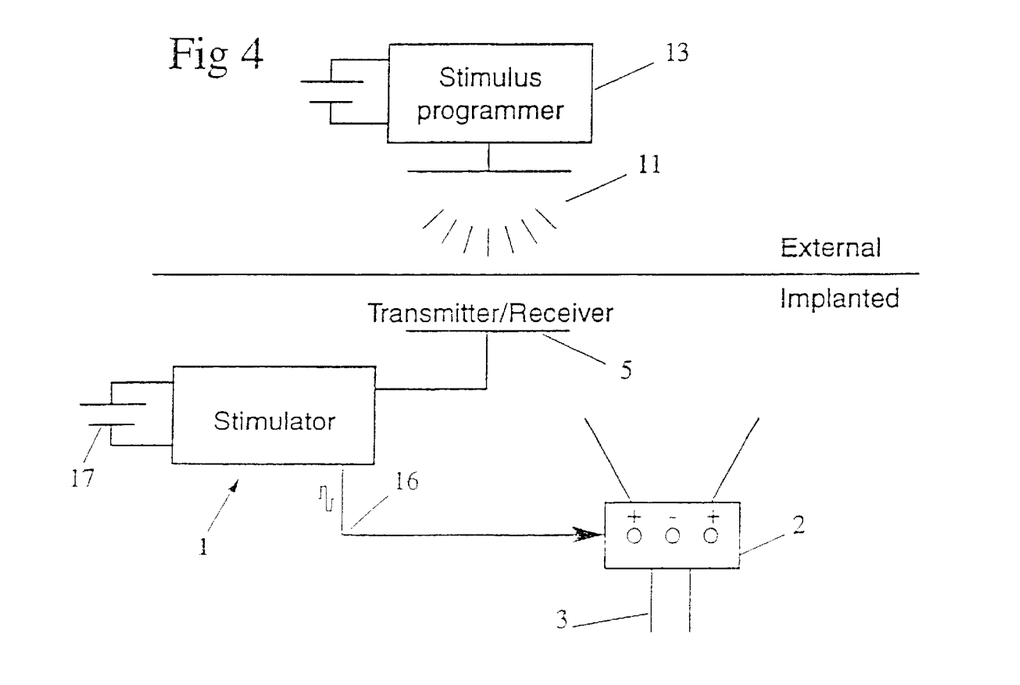
FIG. 4 illustrates a sphincter stimulator programming unit and sphincter stimulator of the system of FIG. 1.

As is best illustrated in FIG. 4, RF transceiver 5 of stimulator 1 is communicable with a third output of processing unit 4 for transmitting sphincter stimulator telemetry information indicative of one or more the parameters of the sphincter stimulator for remote detection. The information is transmitted by radio frequency signals, however, in other embodiments of the invention the sphincter stimulator information is transmitted by microwave means, optical means or by magnetic energy. The sphincter stimulator information signal includes information regarding parameters such as stimulation signal-frequency, current, width and/or shape, and received signal strength and battery status. This is useful for use in a controller intended for use by physicians.

A remote sphincter stimulator programming unit 13 is adapted to receive the sphincter stimulator information provided by receiver 5. The sphincter stimulator programming unit includes a transceiver 14 for providing a calibration signal to stimulator 1 which, in response, selectively varies one or more of the output properties of stimulator 1. The calibration signal is preferably transmitted in response to receiving the sphincter stimulator telemetry information. The calibration signal includes coding to selectively vary the output current, shape, frequency and/or width. Conveniently, the remote sphincter stimulator programming unit is integrated into the physician controller.

The preferred embodiments of the invention also provide a method of treating urinary incontinence in a person including the steps of disposing the implanted smooth muscle sphincter substantially around a urethra, locating a plurality of electrodes in predetermined locations in the sphincter and electrically connecting them with an implanted sphincter stimulator as hereinbefore described.

The sphincter stimulator is then selectively actuated on receipt of the control signal to provide the predetermined stimulation signal to either contract the sphincter or allow it to relax. The method includes providing the stimulation signal to contract the urethra or allow it to relax from output 6 of sphincter stimulator 1. In other embodiments of the invention, however, the stimulation signal to contract the sphincter about the urethra is provided by a separate output of sphincter stimulator 1 to that which provides a stimulation signal to allow the urethra to relax.

There is also provided a method of surgically implanting a sphincter stimulator system as hereinbefore described in a person for treating incontinence, the method including the steps of implanting the smooth muscle sphincter substantially about the urethra in a person, implanting the sphincter stimulator in the person proximal to the implanted sphincter and implanting electrodes into the sphincter at predetermined locations and electrically connecting the sphincter stimulator with the smooth muscle sphincter.

Other preferred embodiments provide a stimulus system including circuit means defining a single channel electrical pulse generator, power supply means, a control circuit to allow a transplanted sphincter to relax, a separate control circuit to adjust pulse parameters, two or more stimulus electrodes, and leads connecting the stimulator to the electrodes.

The prosthetic sphincter includes a sheath of innervated or reinnervatable muscle tissue taken from the selected muscle and transplanted around the urethra. In one embodiment, a segment of distal small intestine, 2–3 cm long, on a vascular pedicle is isolated and the remaining intestine is rejoined by end to end anastomosis. The isolated segment is opened along its antimesenteric border and the mucosa is dissected away.

The isolated segment is drawn down to the neck of the bladder. It is then taken around the bladder neck, so that the circular muscle is disposed substantially circumferentially with respect to the neck, and the cut antimesenteric borders are sewn together to create a close fit around the neck of the bladder. If necessary, the circumferential length is reduced to create a close fit. The newly created and vascularised sphincter is secured in place by sewing it to the superficial connective tissue of the bladder neck. A stimulating electrode assembly is sewn to the transplanted intestine, with the axis of the electrode assembly at right angles to the circular muscle, adjacent to the entry of the vessels from the vascular pedicle. The anchoring ligatures penetrate the sphincter and are secured to the underlying bladder neck.

In an alternative embodiment, the sphincter augmentation is made by dissecting the anococcygeus muscles from their spinal insertions, and drawing the freed muscle around the bladder neck. The sphincter may also be created from a section of muscular vein, venous smooth muscle, the terminal ilium and transplanted as a segment devoid of mucosa and having its circulation intact, or the dartos smooth muscle from the scrotum or labia.

The stimulus pulse generator transfers electrical pulses to the electrodes and these pulses are converted into action potentials in the nerves transplanted with the muscle sphincter or in the nerves which re-innervate the sphincter after surgery.

All implanted circuitry is preferably sealed and encased in a biologically inert material such as a biocompatible silicone material. The metallic electrodes and leads are preferably of Platinum-Iridium alloy. The connecting wires are preferably insulated with a silicone coating and lead to an implanted control unit placed between the abdominal muscle and skin.

The stimulator is required to maintain continuous tone in the transplanted sphincter sufficient to hold urine in the bladder without leakage by continuous stimulation. To release urine, an external control unit using, for example, a radio frequency signal will turn off the internal unit to halt the stimulation of the sphincter, and is shown schematically in FIG. 3.

Alterative embodiments of the invention employ microwave or optical means, for example, in the form of infra-red radiation, to communicate the control signal to the sphincter stimulator, and the sphincter stimulator includes a corresponding receiver at or near the skin of the person.

The person would hold the external device adjacent the skin over the implant (and push an actuation button) to allow the transplanted sphincter to relax and urine to flow. After bladder emptying, the patient would then push the button again to resume sphincteric pressure. As described, if the user forgets to push the button to close the sphincter, the stimulator could be programmed to resume operation automatically after a given time.

The advantages of this system are twofold. Firstly, the patient does not need to hold the external control unit against their skin for the whole period of bladder emptying. They simply initiate the process and can then put the unit aside if desired. The second advantage is that such a system allows the stimulator circuitry to be adjusted externally.

In embodiments where the signal is communicated magnetically, a permanent magnet is placed on the surface of the skin directly over the location of the implanted control circuit. The circuit is designed to detect the presence of the magnetic field and shut off the stimulation accordingly. To empty the bladder, therefore, the person simply places a magnet over the implant for the time period required to empty the bladder. A small permanent magnet is a convenient item to carry around and requires no batteries. One disadvantage of such a system is that a magnetic detector needs to be added to the implanted device and this, in turn, requires more power from the internal batteries.

It is envisaged that the requirements of the stimulator may change, both post-operatively and with alteration of the preserved sphincteric resistance as the person ages. Access to the implanted device via surgery for the purpose of hardware adjustment is, of course, undesirable. Therefore, adjustment of the stimulus parameters via an external radio link to the sphincter stimulator programming unit 13 is a preferred feature of the system.

It will be appreciated that various modifications and alterations may be made to the system described above without departing from the scope and spirit of the invention.

What is claimed is:

1. An implantable sphincter stimulator configured for operatively providing electrical stimulation to a surgically implanted innervated smooth muscle sphincter disposed about a urethra so as to control the flow of urine therethrough, the stimulator including:
   a stimulus generating unit in electrical communication with a receiver, the stimulus generating unit operatively configured to provide a first predetermined electrical stimulation signal adapted to contract said sphincter, and a second predetermined signal adapted to allow said sphincter to relax, one of said predetermined signals being selected in response to a control signal received at the receiver from a remote controller.

2. A sphincter stimulator according to claim 1 wherein the stimulation signal is pulsatile.

3. A sphincter stimulator according to claim 2 wherein the stimulation signal is generally rectangular and symmetrical biphasic.

4. A sphincter stimulator according to claim 2 wherein the stimulation signal current is less than or equal to 30 mA.

5. A sphincter stimulator according to claim 2 wherein the stimulation signal pulse frequency is in the range of 0.25 to 2.5 Hz.

6. A sphincter stimulator according to claim 2 wherein the stimulation signal pulse has a width in the range of 0.05 to 0.20 milliseconds.

7. A sphincter stimulator according to claim 1 wherein the stimulation signal is such as to provide a continuous tone in said sphincter.

8. A sphincter stimulator according to claim 7 wherein the stimulation signal is pulsatile.

9. A sphincter stimulator according to claim 8 wherein the stimulation signal is generally rectangular and symmetrical biphasic.

10. A sphincter stimulator according to claim 8 wherein the stimulation signal current is less than or equal to 30 mA.

11. A sphincter stimulator according to claim 8 wherein the stimulation signal pulse frequency is in the range of 0.25 to 2.5 Hz.

12. A sphincter stimulator according to claim 8 wherein the stimulation signal pulse has a width in the range of 0.05 to 0.20 milliseconds.

13. A sphincter stimulator according to claim 1 wherein the control signal is communicated optically, magnetically, by RF, or by microwave.

14. A sphincter stimulator according to claim 1 wherein the stimulus generating unit includes a demodulator responsive to the received signal for providing a modulated signal to a stimulus encoder which in turn provides a signal to a stimulus driver which provides the stimulation signal at selected ones of the stimulator outputs.

15. A sphincter stimulator according to claim 1 wherein, after the sphincter has relaxed, the stimulator includes means to supply the first stimulation signal at a selected one of its outputs to contract the sphincter when a predetermined signal to contract the sphincter is not received by the receiver for a predetermined period.

16. A sphincter stimulator according to claim 1 including a transmitter for transmitting sphincter stimulator telemetry information indicative of one or more parameters of the stimulator for detection remotely.

17. A sphincter stimulator according to claim 16 wherein the telemetry information is transmitted by the same communications means as the control signal.

18. A sphincter stimulator according to claim 16 wherein the parameters include one or more of the stimulation signal frequency, current, width and/or shape, or received signal strength or battery status.

19. A sphincter stimulator according to claim 16 wherein the receiver is configured to accept a remotely generated sphincter stimulator calibration signal and in response, a signal processing unit selectively varies one or more of the output properties of the sphincter stimulator.

20. A sphincter stimulator according to claim 19 wherein the calibration signal is transmitted in response to received sphincter stimulator telemetry information.

21. A sphincter stimulator according to claim 1 wherein the stimulation generating unit is operatively connected to the sphincter by one or more electrical leads, each having one or more electrodes.

22. A sphincter stimulator according to claim 21 wherein the one or more leads include three electrodes disposed in an epimysal configuration about the sphincter.

23. A sphincter stimulator according to claim 21 wherein the one or more leads include three electrodes disposed in a cuff configuration about the sphincter.

24. A sphincter stimulator according to claim 21 wherein the one or more leads include three electrodes disposed in a tripolar configuration about the sphincter.

25. A system for use in treating urinary incontinence in a person, the system including:
   a portion of innervated smooth muscle tissue configured to define a sphincter and implanted substantially circumferentially about the urethra of the person;
   an implanted sphincter stimulator arranged so as to allow electrical stimuli to be applied to the sphincter; and
   a non-implanted controller in communication with the sphincter stimulator for selectively triggering the generation of predetermined electrical stimulation signals to respectively contract the sphincter or allow the sphincter to relax.

26. A system according to claim 25 wherein the muscle is in the form of a strip.

27. A system according to claim 26 wherein the strip is generally rectangular.

28. A system according to claim 25 wherein the muscle is disposed substantially fully around the urethra in a generally cylindrical arrangement.

29. A system according to claim 28 wherein the long axes of the muscle cells are substantially circumferentially aligned.

30. A system according to claim 25 wherein the smooth muscle is taken from the terminal ileum and transplanted about the urethra as a segment devoid of mucosa and having its circulation intact.

31. A system according to claim 30 wherein the muscle is in the form of a strip.

32. A system according to claim 31 wherein the strip is generally rectangular.

33. A system according to claim 32 wherein the strip has dimensions in the range from 4.5 cm to 7.5 cm by 1.25 cm to 2.25 cm.

34. A system according to claim 25 wherein the muscle is venous smooth muscle.

35. A system according to claim 34 wherein the muscle is in the form of a strip.

36. A system according to claim 35 wherein the strip is generally rectangular.

37. A system according to claim 36 wherein the strip has dimensions in the range from 4.5 cm to 7.5 cm by 1.25 cm to 2.25 cm.

38. A system according to claim 25 wherein the muscle is anococcygeus smooth muscle.

39. A system according to claim 38 wherein the muscle is in the form of a strip.

40. A system according to claim 39 wherein the strip is generally rectangular.

41. A system according to claim 40 wherein the strip has dimensions in the range from 4.5 cm to 7.5 cm by 1.25 cm to 2.25 cm.

42. A system according to claim 25 wherein the muscle is smooth muscle from the bladder.

43. A system according to claim 42 wherein the muscle is in the form of a strip.

44. A system according to claim 43 wherein the strip is generally rectangular.

45. A system according to claim 44 wherein the strip has dimensions in the range from 4.5 cm to 7.5 cm by 1.25 cm to 2.25 cm.

46. A system according to claim 25 wherein the muscle is the dartos muscle taken from the scrotum or labia.

47. A system according to claim 46 wherein the muscle is in the form of a strip.

48. A system according to claim 47 wherein the strip is generally rectangular.

49. A system according to claim 48 wherein the muscle strip has the dimensions of 6 cm by 1.5 to 2 cm.

50. A system according to claim 25 wherein the sphincter stimulator includes a stimulus generating unit in electrical communication with a receiver, the stimulus generating unit operatively configured to provide a first predetermined electrical stimulation signal adapted to contract said sphincter, and a second predetermined signal adapted to allow said sphincter to relax, one of said predetermined signals being selected in response to a control signal received at the receiver from a remote controller.

51. A system according to claim 50 wherein the stimulation signal is pulsatile.

52. A system according to claim 51 wherein the stimulation signal is generally rectangular and symmetrical biphasic.

53. A system according to claim 51 wherein the stimulation signal current is less than or equal to 30 mA.

54. A system according to claim 51 wherein the stimulation signal pulse frequency is in the range of 0.25 to 2.5 Hz.

55. A system according to claim 51 wherein the stimulation signal pulse has a width in the range of 0.05 to 0.20 milliseconds.

56. A system according to claim 50 wherein the stimulation signal is such as to provide a continuous tone in said sphincter.

57. A system according to claim 56 wherein the stimulation signal is pulsatile.

58. A system according to claim 57 wherein the stimulation signal is generally rectangular and symmetrical biphasic.

59. A system according to claim 57 wherein the stimulation signal current is less than or equal to 30 mA.

60. A system according to claim 57 wherein the stimulation signal pulse frequency is in the range of 0.25 to 2.5 Hz.

61. A system according to claim 57 wherein the stimulation signal pulse has a width in the range of 0.05 to 0.02 milliseconds.

62. A system according to claim 50 wherein the control signal is communicated optically, magnetically, by RF, or by microwave.

63. A system according to claim 50 wherein the stimulus generating unit includes a demodulator responsive to the received signal for providing a modulated signal to a stimulus encoder which in turn provides a signal to a stimulus driver which provides the stimulation signal at selected ones of the stimulator outputs.

64. A system according to claim 50 wherein, after the sphincter has relaxed, the stimulator includes means to supply the first stimulation signal at a selected one of its outputs to contract the sphincter when a predetermined signal to contract the sphincter is not received by the receiver for a predetermined period.

65. A system according to claim 50 including a transmitter for transmitting sphincter stimulator telemetry information indicative of one or more parameters of the stimulator for detection remotely.

66. A system according to claim 65 wherein the telemetry information is transmitted by the same communications means as the control signal.

67. A system according to claim 65 wherein the parameters include one or more of the stimulation signal frequency, current, width and/or shape, or received signal strength or battery status.

68. A system according to claim 65 wherein the receiver is configured to accept a remotely generated sphincter stimulator calibration signal and in response, a signal processing unit selectively varies one or more of the output properties of the sphincter stimulator.

69. A system according to claim 68 wherein the calibration signal is transmitted in response to received sphincter stimulator telemetry information.

70. A system according to claim 50 wherein the stimulation generating unit is operatively connected to the sphincter by one or more electrical leads, each having one or more electrodes.

71. A system according to claim 70 wherein the one or more leads include three electrodes disposed in an epimysal configuration about the sphincter.

72. A system according to claim 70 wherein the one or more leads include three electrodes disposed in a cuff configuration about the sphincter.

73. A system according to claim 70 wherein the one or more leads include three electrodes disposed in a tripolar configuration about the sphincter.

74. A system according to claim 25 wherein the controller includes:
   a transmitter;
   means for generating a predetermined control signal at the transmitter;
   a power source; and
   actuation means for selectively generating the control signal such that on receipt of the signal, the sphincter stimulator provides the stimulation signal at its output in order to contract the sphincter or allow it to relax.

75. A system according to claim 25 wherein the controller includes a receiver for receiving a stimulator information telemetry signal from the sphincter stimulator.

76. A system according to claim 74 wherein the control signal is transmitted optically, magnetically, by radio waves, or by microwaves.

77. A system according to claim 74 including a remote sphincter stimulator programming unit for selectively programming the sphincter stimulator to provide a predetermined output in response to the control signal.

78. A system according to claim 77 wherein one or more of the stimulation signal current, shape, frequency and width is variable in response to a calibration signal provided by the programming unit.

79. A system according to claim 77 wherein the programming unit includes a transceiver for providing the programming signal to the stimulator.

80. A system according to claim 77 wherein the programming unit is the controller.

81. A method of using an implantable sphincter stimulator for treating urinary incontinence, the method including the steps of disposing a smooth muscle sphincter about a urethra, providing an implanted stimulator unit connected to electrodes, arranging the electrodes so that the electrodes are adapted to stimulate the neural structures of said sphincter, and providing a predetermined stimulation signal at the sphincter stimulator output to either contract the sphincter or allow it to relax in response to a control signal provided from an externally disposed controller.

82. A method according to claim 81 wherein the stimulation signal is pulsatile.

83. A method according to claim 82 wherein the stimulation signal is generally rectangular and symmetrically biphasic.

84. A method according to claim 82 wherein the stimulation signal current is less than 30 mA.

85. A method according to claim 82 wherein the stimulation signal pulses are provided with a frequency on the range of 0.25 to 2.0 Hz.

86. A method according to claim 82 wherein the stimulation signal pulse width is in the range of 0.05 to 0.02 milliseconds.

87. A method according to claim 81 wherein the stimulation signal is such as to provide a continuous tone in said sphincter.

88. A method according to claim 87 wherein the stimulation signal is pulsatile.

89. A method according to claim 88 wherein the stimulation signal is generally rectangular and symmetrically biphasic.

90. A method according to claim 88 wherein the stimulation signal current is less than 30 mA.

91. A method according to claim 88 wherein the stimulation signal pulses are provided with a frequency on the range of 0.25 to 2.0 Hz.

92. A method according to claim 88 wherein the stimulation signal pulse width is in the range of 0.05 to 0.02 milliseconds.

93. A method according to claim 81 including the step of transmitting the control signal to the sphincter stimulator by any one of microwaves, radio waves, optical signals or magnetic energy.

94. A method according to claim 81 including the step of arranging three electrodes in contact with the sphincter in an epimysal configuration.

95. A method according to claim 81 including the step of arranging three electrodes in contact with the sphincter in a cuff configuration.

96. A method according to claim 81 including the step of arranging three electrodes in contact with the sphincter in a tripolar configuration.

97. A method of treating urinary incontinence including the steps of:
disposing an implanted innervated smooth muscle sphincter around a urethra;
locating a plurality of electrodes in predetermined locations in the sphincter in electrically connecting the electrodes with an implanted sphincter stimulator; and
selectively actuating the sphincter stimulator to provide a predetermined stimulation signal to either contract the urethra or allow it to relax in response to a remotely generated control signal.

98. A method according to claim 97 wherein the sphincter stimulator includes a stimulus generating unit in electrical communication with a receiver, the stimulus generating unit operatively configured to provide a first predetermined electrical stimulation signal adapted to contract said sphincter, and a second predetermined signal adapted to allow said sphincter to relax, one of said predetermined signals being selected in response to a control signal received at the receiver from a remote controller.

99. A method according to claim 98 wherein the stimulation signal is pulsatile.

100. A method according to claim 99 wherein the stimulation signal is generally rectangular and symmetrical biphasic.

101. A method according to claim 99 wherein the stimulation signal current is less than or equal to 30 mA.

102. A method according to claim 99 wherein the stimulation signal pulse frequency is in the range of 0.25 to 2.5 Hz.

103. A method according to claim 99 wherein the stimulation signal pulse has a width in the range of 0.05 to 0.02 milliseconds.

104. A method according to claim 98 wherein the stimulation signal is such as to provide a continuous tone in said sphincter.

105. A method according to claim 104 wherein the stimulation signal is pulsatile.

106. A method according to claim 105 wherein the stimulation signal is generally rectangular and symmetrical biphasic.

107. A method according to claim 105 wherein the stimulation signal current is less than or equal to 30 mA.

108. A method according to claim 105 wherein the stimulation signal pulse frequency is in the range of 0.25 to 2.5 Hz.

109. A method according to claim 105 wherein the stimulation signal pulse has a width in the range of 0.05 to 0.02 milliseconds.

110. A method according to claim 98 wherein the control signal is communicated optically, magnetically, by RF, or by microwave.

111. A method according to claim 98 wherein the stimulus generating unit includes a demodulator responsive to the received signal for providing a modulated signal to a stimulus encoder which in turn provides a signal to a stimulus driver which provides the stimulation signal at selected ones of the stimulator outputs.

112. A method according to claim 98 wherein, after the sphincter has relaxed, the stimulator includes means to supply the first stimulation signal at a selected one of its outputs to contract the sphincter when a predetermined signal to contract the sphincter is not received by the receiver for a predetermined period.

113. A method according to claim 98 wherein said sphincter stimulator includes a transmitter for transmitting sphincter stimulator telemetry information indicative of one or more parameters of the stimulator for detection remotely.

114. A method according to claim 113 wherein the telemetry information is transmitted by the same communications means as the control signal.

115. A method according to claim 113 wherein the parameters include one or more of the stimulation signal frequency, current, width and/or shape, or received signal strength or battery status.

116. A method according to claim 113 wherein the receiver is configured to accept a remotely generated sphincter stimulator calibration signal and in at response, a signal processing unit selectively varies one or more of the output properties of the sphincter stimulator.

117. A method according to claim 116 wherein the calibration signal is transmitted in response to received sphincter stimulator telemetry information.

118. A method according to claim 98 wherein the stimulation generating unit is operatively connected to the sphincter by one or more electrical leads, each having one or more electrodes.

119. A method according to claim 118 wherein the one or more leads include three electrodes disposed in an epimysal configuration about the sphincter.

120. A method according to claim 118 wherein the one or more leads include three electrodes disposed in a cuff configuration about the sphincter.

121. A method according to claim 118 wherein the one or more leads include three electrodes disposed in a tripolar configuration about the sphincter.

122. A method of surgically implanting a sphincter stimulator system for treating urinary incontinence including the steps of:
implanting a smooth muscle sphincter about the urethra in a person;
implanting a stimulator proximal to the sphincter; and
implanting a plurality of electrodes into the sphincter at predetermined locations and electrically connecting the stimulator therewith.

123. A method according to claim 122 wherein the system includes:
a portion of inervated smooth muscle tissue configured to define a sphincter and implanted substantially circumferentially about the urethra of the person;
an implanted sphincter stimulator arranged so as to allow electrical stimuli to be applied to the sphincter; and
a non-implanted controller in communication with the sphincter stimulator for selectively triggering the generation of predetermined electrical stimulation signals to respectively contract the sphincter or allow the sphincter to relax.

124. A method according to claim 123 wherein the muscle is in the form of a strip.

125. A method according to claim 124 wherein the strip is generally rectangular.

126. A method according to claim 123 wherein the muscle is disposed substantially fully around the urethra in a generally cylindrical arrangement.

127. A method according to claim 126 wherein the long axes of the muscle cells are substantially circumferentially aligned.

128. A method according to claim 123 wherein the smooth muscle is taken from the terminal ileum and transplanted about the urethra as a segment devoid of mucosa and having its circulation intact.

129. A method according to claim 128 wherein the muscle is in the form of a strip.

130. A method according to claim 129 wherein the strip is generally rectangular.

131. A method according to claim 130 wherein the strip has dimensions in the range from 4.5 cm to 7.5 cm by 1.25 cm to 2.25 cm.

132. A method according to claim 123 wherein the muscle is venous smooth muscle.

133. A method according to claim 132 wherein the muscle is in the form of a strip.

134. A method according to claim 133 wherein the strip is generally rectangular.

135. A method according to claim 134 wherein the strip has dimensions in the range from 4.5 cm to 7.5 cm by 1.25 cm to 2.25 cm.

136. A method according to claim 123 wherein the muscle is anococcygeus smooth muscle.

137. A method according to claim 136 wherein the muscle is in the form of a strip.

138. A method according to claim 137 wherein the strip is generally rectangular.

139. A method according to claim 137 wherein the strip has dimensions in the range from 4.5 cm to 7.5 cm by 1.25 cm to 2.25 cm.

140. A method according to claim 123 wherein the muscle is smooth muscle from the bladder.

141. A method according to claim 140 wherein the muscle is in the form of a strip.

142. A method according to claim 141 wherein the strip is generally rectangular.

143. A method according to claim 142 wherein the strip has dimensions in the range from 4.5 cm to 7.5 cm by 1.25 cm to 2.25 cm.

144. A method according to claim 123 wherein the muscle is the dartos muscle taken from the scrotum or labia.

145. A method according to claim 144 wherein the muscle is in the form of a strip.

146. A method according to claim 145 wherein the strip is generally rectangular.

147. A method according to claim 146 wherein the muscle strip has the dimensions of 6 cm by 1.5 to 2 cm.

148. A method according to claim 123 wherein the sphincter stimulator includes a stimulous generating unit in electrical communication with a receiver, the stimulus generating unit operatively configured to provide a first predetermined electrical stimulation signal adapted to contract said sphincter, and a second predetermined signal adapted to allow said sphincter to relax, one of said predetermined signals being selected in response to a control signal received at the receiver from a remote controller.

149. A method according to claim 148 wherein the stimulation signal is pulsatile.

150. A method according to claim 149 wherein the stimulation signal is generally rectangular and symmetrical biphasic.

151. A method according to claim 149 wherein the stimulation signal current is less than or equal to 30 mA.

152. A method according to claim 149 wherein the stimulation signal pulse frequency is in the range of 0.25 to 2.5 Hz.

153. A method according to claim 149 wherein the stimulation signal pulse has a width in the range of 0.05 to 0.02 milliseconds.

154. A method according to claim 148 wherein the stimulation signal is such as to provide a continuous tone in said sphincter.

155. A method according to claim 154 wherein the stimulation signal is pulsatile.

156. A method according to claim 155 wherein the stimulation signal is generally rectangular and symmetrical biphasic.

157. A method according to claim 155 wherein the stimulation signal current is less than or equal to 30 mA.

158. A method according to claim 155 wherein the stimulation signal pulse frequency is in the range of 0.25 to 2.5 Hz.

159. A method according to claim 155 wherein the stimulation signal pulse has a width in the range of 0.05 to 0.02 milliseconds.

160. A method according to claim 148 wherein the control signal is communicated optically, magnetically, by RF, or by microwave.

161. A method according to claim 148 wherein the stimulous generating unit includes a demodulator responsive to the received signal for providing a modulated signal to a stimulus encoder which in turn provides a signal to a stimulus driver which provides the stimulation signal at selected ones of the stimulator outputs.

162. A method according to claim 148 wherein, after the sphincter has relaxed, the stimulator includes means to supply the first stimulation signal at a selected one of its outputs to contract the sphincter when a predetermined signal to contract the sphincter is not received by the receiver for a predetermined period.

163. A method according to claim 148 wherein said system includes a transmitter for transmitting sphincter stimulator telemetry information indicative of one or more parameters of the stimulator for detection remotely.

164. A method according to claim 163 wherein the telemetry information is transmitted by the same communications means as the control signal.

165. A method according to claim 163 wherein the parameters include one or more of the stimulation signal frequency, current, width and/or shape, or received signal strength or battery status.

166. A method according to claim 163 wherein the receiver is configured to accept a remotely generated sphincter stimulator calibration signal and in response, a signal processing unit selectively varies one or more of the output properties of the sphincter stimulator.

167. A method according to claim 166 wherein the calibration signal is transmitted in response to received sphincter telemetry information.

168. A method according to claim 148 wherein the stimulation generating unit is operatively connected to the sphincter by one or more electrical leads, each having one or more electrodes.

169. A method according to claim 168 wherein the one or more leads include three electrodes disposed in an epimysal configuration about the sphincter.

170. A method according to claim 168 wherein the one or more leads include three electrodes disposed in a cuff configuration about the sphincter.

171. A method according to claim 168 wherein the one or more leads include three electrodes disposed in a tripolar configuration about the sphincter.

172. A method according to claim 123 wherein the controller includes:

a transmitter;

means for generating a predetermined control signal at the transmitter;

a power source; and actuation means for selectively generating the control signal such that on receipt of the signal, the sphincter stimulator provides the stimulation signal at its output in order to contract the sphincter or allow it to relax.

173. A method according to claim 123 wherein the controller includes a receiver for receiving a stimulator information telemetry signal from the sphincter stimulator.

174. A method according to claim 172 wherein control signal is transmitted optically, magnetically, by radio waves, or by microwaves.

175. A method according to claim 172 wherein the system includes a remote sphincter stimulator programming unit for selectively programming the sphincter stimulator to provide a predetermined output in response to the control signal.

176. A method according to claim 175 wherein one or more of the stimulation signal current, shape, frequency and width is variable in response to a calibration signal provided by the programming unit.

177. A method according to claim 175 wherein the programming unit includes a transceiver for providing the programming signal to the stimulator.

178. A method according to claim 175 wherein the programming unit is the controller.

* * * * *

UNITED STATES PATENT AND TRADEMARK OFFICE
CERTIFICATE OF CORRECTION

PATENT NO. : 6,659,936 B1
DATED : December 9, 2003
INVENTOR(S) : Furness et al.

It is certified that error appears in the above-identified patent and that said Letters Patent is hereby corrected as shown below:

Column 13,
Line 66, delete "0.02" and replace with -- 0.20 --.

Column 15,
Lines 30 and 46, delete "0.02" and replace with -- 0.20 --.

Column 16,
Lines 24 and 41, delete "0.02" and replace with -- 0.20 --.

Column 18,
Lines 51 and 67, delete "0.02" and replace with -- 0.20 --.

Signed and Sealed this

Twenty-fourth Day of January, 2006

JON W. DUDAS
*Director of the United States Patent and Trademark Office*